United States Patent
Carter

(10) Patent No.: US 6,896,667 B2
(45) Date of Patent: May 24, 2005

(54) FOOT AND HAND TREATMENT SYSTEM

(76) Inventor: Linda A. Carter, 3630 W. Country Club Dr., Irving, TX (US) 75038

(*) Notice: Subject to any disclaimer, the term of this patent is extended or adjusted under 35 U.S.C. 154(b) by 78 days.

(21) Appl. No.: 10/375,523

(22) Filed: Feb. 27, 2003

(65) Prior Publication Data

US 2003/0171724 A1 Sep. 11, 2003

Related U.S. Application Data

(60) Provisional application No. 60/360,449, filed on Feb. 27, 2002.

(51) Int. Cl.[7] .............................................. A61M 35/00
(52) U.S. Cl. ...................................... 604/292; 604/293
(58) Field of Search ................................ 604/289, 290, 604/292, 293; 2/158, 159, 164, 169, 161.7; 36/10

(56) References Cited

U.S. PATENT DOCUMENTS

| | | | | | |
|---|---|---|---|---|---|
| 1,941,508 A | * | 1/1934 | Zwicker | ....................... | 66/174 |
| 2,342,547 A | * | 2/1944 | Kuehnel | ........................ | 2/158 |
| 3,896,807 A | * | 7/1975 | Buchalter | .................... | 604/289 |
| 4,122,554 A | * | 10/1978 | Stager | ........................... | 2/164 |
| 4,622,035 A | * | 11/1986 | Palmer et al. | .............. | 604/293 |

OTHER PUBLICATIONS

Dry Skin Relief with Handaid Moisturing Glove and Booties; http://www.robanda.com/skin-care/handaid.html; Feb. 24, 2003.
HandAid Moisturizing Gloves & Booties; http://www.hand-aid.com/foot.tpl; Feb. 24, 2003.
HandAid Moisturizing Gloves & Booties; http://www.hand-aid.com/hand.tpl; Feb. 24, 2003.
Allerderm; http://www.allerderm.com/physicians/specials.asp; 2 pages; Feb. 24, 2003.
Moisturejamzz; http://www.moisturejamzz.com/products.html; Jun. 18, 2002.
Moisturejamzz; http://www.moisturejamzz.com/kit3.html; Jun. 18, 2002.

* cited by examiner

Primary Examiner—Larry I. Schwartz
Assistant Examiner—C. Lynne Anderson
(74) Attorney, Agent, or Firm—Michael A. O'Neal

(57) ABSTRACT

A treatment fluid dispensing apparatus comprises a fluid impervious layer and an overlying treatment fluid dispensing layer. The fluid treatment dispensing layer comprises a finely woven fabric formed from natural or synthetic fibers which normally retains the treatment fluid and which dispensing the treatment fluid responsive to pressure. The treatment fluid dispensing layer is configured to dispense treatment fluid to areas of the hands and feet over a prolonged period of time.

6 Claims, 4 Drawing Sheets

FOOT AND HAND TREATMENT SYSTEM

This application claims the benefit of Provisional Application No. 60/360,449, filed Feb. 27, 2002.

TECHNICAL FIELD

This invention relates generally to the application of fluids to the hands and feet, and more particularly to the application of treatment fluids to the hands and feet over an extended period of time.

BACKGROUND AND SUMMARY OF THE INVENTION

As is well known, persons of all ages benefit from the application of treatment fluids to the hands and feet. As used herein, the term fluid includes liquids, gels, lotions, creams, and all other non-solid flowable materials. The term treatment fluids includes over-the-counter preparations such as moisturizers, sun block fluids, sunburn treatment fluids, anti-itch preparations used in the treatment of insect bites and exposure to poisonous plants, etc. The term treatment fluids also includes preparations prescribed by doctors for the treatment of more serious problems.

The foregoing and other types of treatment fluids almost always require continuous application in order to achieve maximum benefit. However, the daily activities of most people preclude the continuous application of treatment fluids which results either in ineffective treatment or the requirement for frequent re-application of the treatment fluid being used.

The present invention relates to the continuous application of treatment fluids to the hands and feet which overcomes the foregoing and other problems which have long since characterized the prior art. In accordance with the broader aspects of the invention, there is provided a two layer structure, including a first fluid impervious layer which retains a treatment fluid and a second layer formed from a fine mesh of either natural or synthetic fibers which normally retains the treatment fluid but which releases the treatment fluid upon the application of pressure thereto. The treatment fluid dispensing layer may be subdivided in accordance with predetermined patterns better to control the release of treatment fluid therethrough.

In accordance with the first embodiment of the invention, there is provided a treatment fluid dispensing apparatus having the form of the human foot. The foot-shaped fluid treatment dispensing apparatus may comprise part of a sock or bootie which is worn by the person requiring the application of a treatment fluid as the person performs his or her daily activities. Alternatively, the first embodiment of the invention may take the form of a shoe liner or sock liner which is utilized within the shoe that would otherwise be worn by the person requiring the application of the treatment fluid to his or her feet. The first embodiment of the invention may also comprise a foot liner that is received within a sock, bootie, or shoe for engagement with the foot of a person.

In accordance with the second embodiment of the invention, there is provided a treatment fluid dispensing apparatus having the form of the human hand. The second embodiment of the invention is generally configured like a glove which is worn by the person requiring the application of a treatment fluid to the hands as the person goes about his or her daily activities. The second embodiment of the invention may also comprise a partial glove which covers the palm but leaves the fingers and thumb exposed.

BRIEF DESCRIPTION OF THE DRAWINGS

A more complete understanding of the present invention may be had by reference to the following Detailed Description when taken in connection with the accompanying Drawings, wherein.

DETAILED DESCRIPTION

Figure 1:
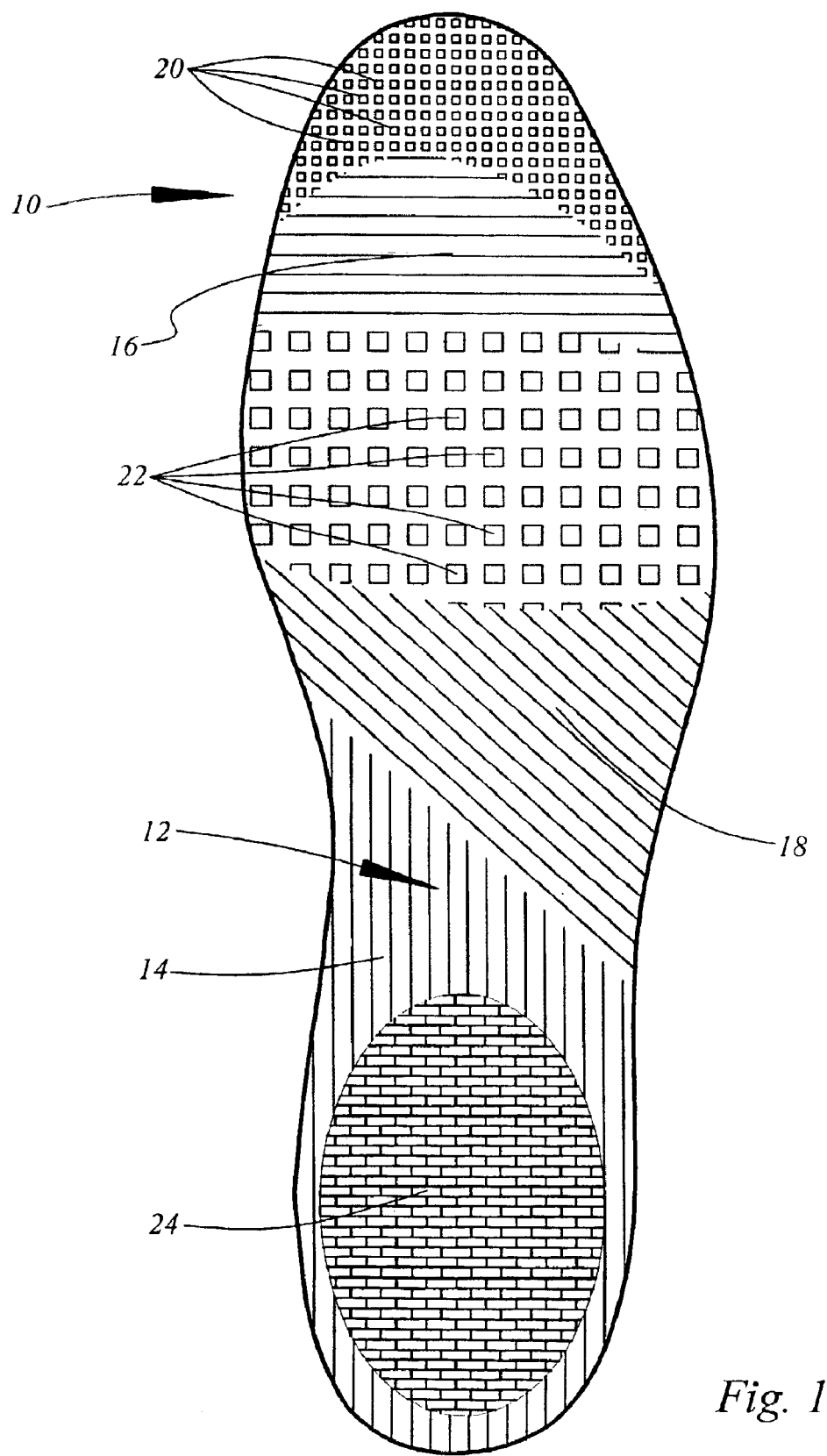
FIG. 1 is an illustration of a first embodiment of the invention.
Figure 2:
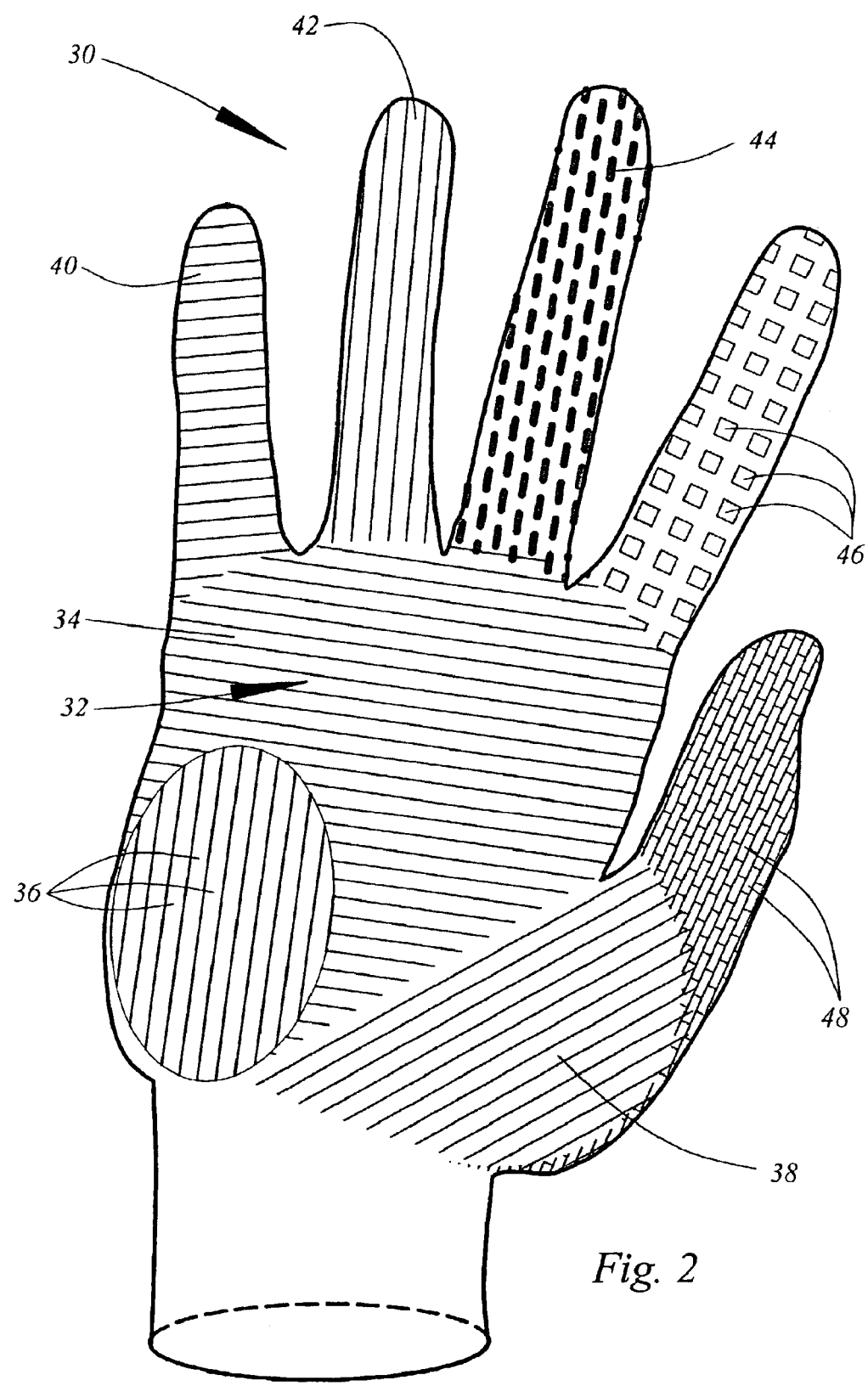
FIG. 2 is perspective view further illustrating the first embodiment of the invention.

Referring now to the Drawings, and particularly to FIGS. 1 and 2 thereof, there is shown an apparatus 10 for applying treatment fluids to the feet comprising the first embodiment of the invention. The apparatus 10 is generally in the shape of a human foot and comprises a fluid impervious layer 11 and a skin engaging fluid dispensing layer 12. The layer 12 is formed from finely woven natural or synthetic fibers, and is configured to normally retain a treatment fluid therein and to cause treatment fluid to flow therethrough upon the application of pressure.

As is best illustrated in FIG. 1, the treatment fluid dispensing layer 12 may take the form of a wide variety of configurations depending upon the requirements of particular applications of the invention. For example, the treatment fluid dispensing layer 12 may comprise spaced, parallel longitudinally extending sections 14; spaced, parallel transversely extending sections 16; or spaced, parallel angularly extending sections 18. The treatment fluid dispensing layer 12 may also be configured to comprise a plurality of small sections 20 each containing a relatively small amount of treatment fluid or a plurality of larger sections 22 each containing a somewhat larger quantity of treatment fluid. FIG. 1 also illustrates the treatment fluid dispensing layer 12 configured in a checkerboard pattern 24 which precisely controls the release of treatment fluid. As will be appreciated by those skilled in the art, the treatment fluid dispensing layer may assume a wide variety of configurations and styles depending on the requirements of particular applications of the invention.

Any of the sections or patterns 14, 16, 18, 20, 22, and 24 comprising the apparatus 10 may comprise a more densely woven portion of the dispensing layer 12 as compared with the weaving of adjacent portions of the layer 12. More densely woven portions of the layer 12 restrict the flow of treatment fluid therethrough, and therefore require the application of greater pressure to effect the dispensing of the same amount of treatment fluid. As will therefore be understood, the use of more densely woven portions of the layer 12 may be appropriate under the heal section or under the section of the layer 12 aligned with the balls of the feet whereas the use of a less dense weave may be appropriate for other portions of the layer 12 which are not likely to subjected to the application of higher pressures.

Referring particularly to FIG. 2, a layer of treatment fluid F is received between the fluid impervious layer 11 and the fluid dispensing layer 12 of the apparatus 10. The treatment fluid F may comprise liquids, gels, lotions, creams, and all other non-solid fluid materials. The treatment fluid F may comprise over-the-counter preparations such as moisturizers, sun block fluids, sunburn treatment fluids, anti-itch preparations, etc. The treatment fluid F may also comprise preparations prescribed by doctors for the treatment of skin-related problems.

FIG. 2 also illustrates a structure S which is used to received the apparatus 10 and to retain the apparatus 10 in engagement of the foot of a person to effect treatment of the skin comprising the sole of the foot. The structure S may comprise a booty, a sock, a slipper, a sandal, or a shoe. In the case of a shoe, the apparatus 10 of the present invention may serve as an insole or a foot liner within the interior of the shoe.

Figure 3:
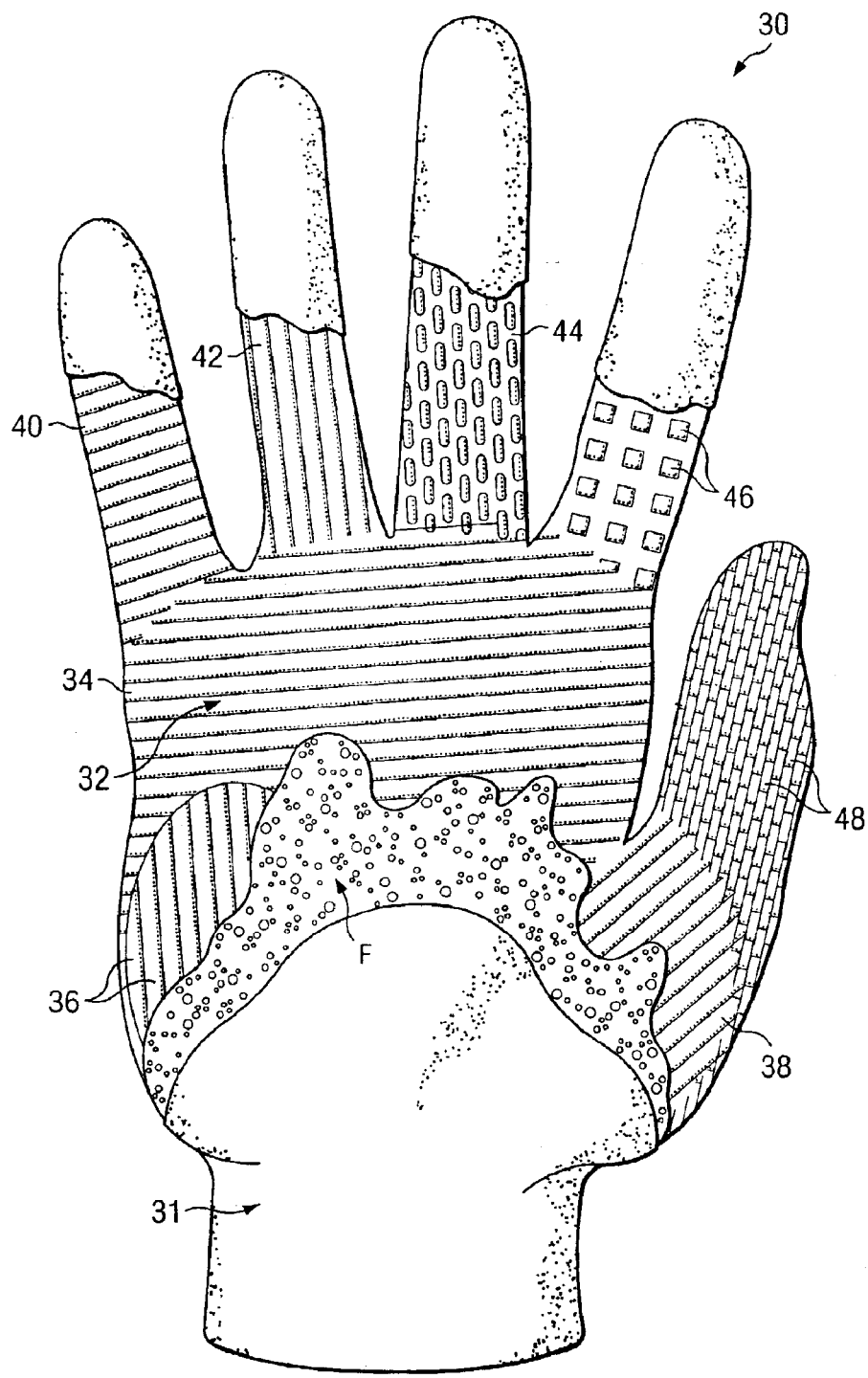
FIG. 3 is an illustration of one side of a second embodiment of the invention.

Referring to FIG. 3, there is shown an apparatus 30 for applying treatment fluids to the human hand comprising the second embodiment of the invention. The apparatus 30 comprises a two layer construction including an overlying fluid impervious layer 31, and a skin engaging underlying fluid dispensing layer 32. The treatment fluid dispensing layer 32 comprises a finely woven fabric formed from natural or synthetic fibers and is adapted to normally retain a treatment fluid while facilitating dispensing of the treatment fluid responsive to pressure.

The treatment fluid dispensing layer 32 may assume a wide variety of configurations. For example, the layer 32 may comprise spaced, parallel transversely extending sections 34; or spaced, parallel longitudinally extending sections 36; or spaced, parallel angularly extending sections 38. Portions of the treatment fluid dispensing layer 32 which are aligned with the fingers may take the form of spaced, parallel transversely extending sections 40 which extend generally around the fingers; or spaced parallel longitudinally extending sections 42 which extend generally along the fingers. The treatment fluid dispensing layer 32 may comprise a generally open configuration which is secured to the overlying fluid impervious layer by a plurality of connection points 44. The treatment fluid dispensing layer 32 may also comprise large or small individual sections 46 configured to dispense smaller amounts of treatment fluid. Another option is to configure the treatment fluid dispensing layer 32 in a checkerboard pattern 48 which affords precise control over the dispensing of treatment through the treatment fluid dispensing layer 32. As will be appreciated by those skilled in the art, the treatment fluid dispensing layer 32 may be configured in a wide variety of configurations depending upon the requirements of particular applications of the invention.

Any of the sections or patterns 34, 36, 38, 40, 42, 46, and 48 comprising the apparatus 30 may comprise a more densely woven portion of the dispensing layer 32 as compared with the weaving of adjacent portions of the layer 32. More densely woven portion of the layer 32 restrict the flow of treatment fluid therethrough, and therefore require the application of greater pressure to effect the dispensing of the same amount of treatment fluid. As will therefore be understood, the use of more densely woven portions of the layer 32 may be appropriate at the tips of the fingers and thumb whereas the use of a less dense weave may be appropriate for other portions of the layer 32 which are not likely to subjected to the application of higher pressures.

A layer of treatment fluid F is received between the fluid impervious layer 31 and the fluid dispensing layer 32 of the apparatus 30. The treatment fluid F may comprise liquids, gels, lotions, creams, and all other non-solid fluid materials. The treatment fluid F may comprise over-the-counter preparations such as moisturizers, sun block fluids, sunburn treatment fluids, anti-itch preparations, etc. The treatment fluid F may also comprise preparations prescribed by doctors for the treatment of skin-related problems.

Figure 4:
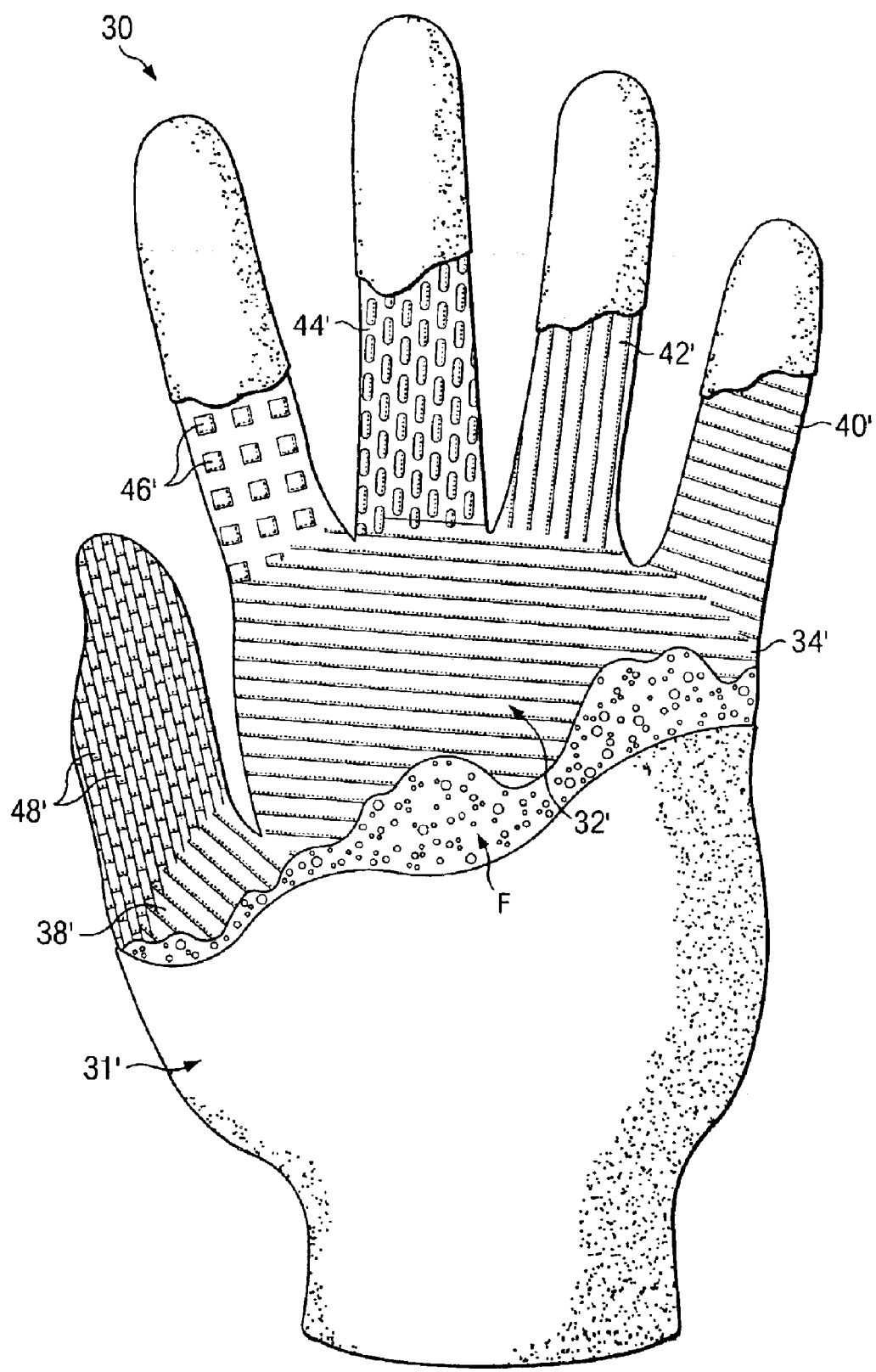
FIG. 4 is an illustration of the opposite side of the second embodiment of the invention.

FIG. 4 illustrates the opposite side of the apparatus 30 for applying treatment fluids to the human hand as illustrated in FIG. 3 and described hereinabove in conjunction therewith. Many of the component parts of the opposite side of the apparatus 30 are identical in construction and function to component parts of the apparatus 30 as illustrated in FIG. 3. Such identical components are designated in FIG. 4 with the same reference numerals utilized above in the description of the apparatus 30 as shown in FIG. 3, but are differentiated therefrom by a prime (') designation.

If the application of treatment fluid is to be confined to the palm of the hand, the opposite side of the apparatus 30 may comprise a liquid impervious layer 31'. However, if treatment fluid is to be applied to both sides of the hand, the opposite side of the apparatus 30 further includes a fluid dispensing layer 32'.

It will therefore be understood that the present invention comprises a structure which extends across the hands or feet of an individual to effect the application of treatment fluids thereto. A treatment fluid dispensing layer normally retains the treatment fluid to be applied, but responds to the application of pressure to dispense the treatment fluid in controlled amounts. In this manner the treatment fluid is applied to the hands or the feet of an individual over an extended period of time.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

What is claimed is:

1. An apparatus for applying treatment fluids to the hands and feet comprising:

a first fluid impervious layer; and a treatment fluid dispensing layer secured to and overlying the fluid impervious layer;

the treatment fluid dispensing layer comprising a finely woven fabric which normally retains the treatment fluid and which dispenses the treatment fluid in response to pressure;

the treatment fluid dispensing layer being divided into a plurality of sections; and wherein the sections comprising the fluid dispensing layer comprise at least two different orientations.

2. An apparatus for applying treatment fluids to the hands and feet comprising:

a first fluid impervious layer; and a treatment fluid dispensing layer secured to and overlying the fluid impervious layer;

the treatment fluid dispensing layer comprising a finely woven fabric which normally retains the treatment fluid and which dispenses the treatment fluid in response to pressure;

the treatment fluid dispensing layer being divided into a plurality of sections; and comprising at least one section which is woven more densely as compared to the weaving of at least one other section.

3. An apparatus for applying treatment fluids to the human hand comprising:

a fluid impervious layer configured in the shape of a human hand;

a treatment fluid dispensing layer also configured in the shape of a human hand;

the treatment fluid dispensing layer being secured to and overlying the fluid impervious layer;

the treatment fluid dispensing layer comprising a finely woven fabric which normally retains treatment fluid and which dispenses treatment fluid in response to pressure;

the treatment fluid dispensing layer being divided into a plurality of sections which dispense treatment fluid in response to different levels of pressure;

a treatment fluid initially received between the fluid impervious layer and the treatment fluid dispensing layer; and wherein the sections comprising the fluid dispensing layer comprise at least two different orientations.

4. An apparatus for applying treatment fluids to the human hand comprising:

a fluid impervious layer configured in the shape of a human hand;

a treatment fluid dispensing layer also configured in the shape of a human hand;

the treatment fluid dispensing layer being secured to and overlying the fluid impervious layer;

the treatment fluid dispensing layer comprising a finely woven fabric which normally retains treatment fluid and which dispenses treatment fluid in response to pressure;

the treatment fluid dispensing layer being divided into a plurality of sections which dispense treatment fluid in response to different levels of pressure;

a treatment fluid initially received between the fluid impervious layer and the treatment fluid dispensing layer; and comprising at least one section which is woven more densely as compared to the weaving of at least one other section.

5. An apparatus for applying treatment fluids to the human foot comprising:

a fluid impervious layer configured in the shape of a human foot;

a treatment fluid dispensing layer also configured in the shape of a human foot;

the treatment fluid dispensing layer being secured to and overlying the fluid impervious layer;

the treatment fluid dispensing layer comprising a finely woven fabric which normally retains treatment fluid and which dispenses treatment fluid in response to pressure;

the treatment fluid dispensing layer being divided into a plurality of sections which dispense treatment fluid in response to different levels of pressure;

a treatment fluid initially received between the fluid impervious layer and the treatment fluid dispensing layer; and wherein the sections comprising the fluid dispensing layer comprise at least two different orientations.

6. An apparatus for applying treatment fluids to the human foot comprising:

a fluid impervious layer configured in the shape of a human foot;

a treatment fluid dispensing layer also configured in the shape of a human foot;

the treatment fluid dispensing layer being secured to and overlying the fluid impervious layer;

the treatment fluid dispensing layer comprising a finely woven fabric which normally retains treatment fluid and which dispenses treatment fluid in response to pressure;

the treatment fluid dispensing layer being divided into a plurality of sections which dispense treatment fluid in response to different levels of pressure;

a treatment fluid initially received between the fluid impervious layer and the treatment fluid dispensing layer; and comprising at least one section which is woven more densely as compared to the weaving of at least one other section.

* * * * *